United States Patent
Chang et al.

(10) Patent No.: US 9,895,131 B2
(45) Date of Patent: Feb. 20, 2018

(54) METHOD AND SYSTEM OF SCANNER AUTOMATION FOR X-RAY TUBE WITH 3D CAMERA

(71) Applicant: Siemens Healthcare GmbH, Erlangen (DE)

(72) Inventors: Yao-Jen Chang, Princeton, NJ (US);
Vivek Kumar Singh, Princeton, NJ (US); Kai Ma, Plainsboro, NJ (US);
Ralf Nanke, Baerenbruennlein (DE);
Susanne Dornberger, Erlangen (DE);
Terrence Chen, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 252 days.

(21) Appl. No.: 14/881,526

(22) Filed: Oct. 13, 2015

(65) Prior Publication Data
US 2017/0100089 A1    Apr. 13, 2017

(51) Int. Cl.
*A61B 6/00* (2006.01)
*A61B 6/04* (2006.01)

(52) U.S. Cl.
CPC ............ *A61B 6/54* (2013.01); *A61B 6/0492* (2013.01); *A61B 6/461* (2013.01); *A61B 6/469* (2013.01); *A61B 6/488* (2013.01); *A61B 6/544* (2013.01); *A61B 6/545* (2013.01); *A61B 6/582* (2013.01); *A61B 6/4464* (2013.01); *A61B 6/465* (2013.01); *A61B 6/467* (2013.01)

(58) Field of Classification Search
CPC ....... A61B 6/0492; A61B 6/461; A61B 6/469; A61B 6/488; A61B 6/54; A61B 6/582
See application file for complete search history.

(56) References Cited

U.S. PATENT DOCUMENTS

2016/0092078 A1*  3/2016  Braun ................ A61B 6/032
                                                                348/46

OTHER PUBLICATIONS

Sigal, Leonid, et al. "Loose-limbed people: Estimating 3D human pose and motion using non-parametric belief propagation." International journal of computer vision 98.1 (2012): 15-48.
Shotton, Jamie, et al. "Real-time human pose recognition in parts from single depth images." Communications of the ACM 56.1 (2013): 116-124.
Rusu, Radu Bogdan, and Steve Cousins. "3d is here: Point cloud library (pcl)." Robotics and automation (ICRA), 2011 IEEE International Conference on. IEEE, 2011.
Tu, Zhuowen. "Probabilistic boosting-tree: Learning discriminative models for classification, recognition, and clustering." Computer Vision, 2005. ICCV 2005. Tenth IEEE International Conference on. vol. 2. IEEE, 2005.

* cited by examiner

*Primary Examiner* — Dani Fox

(57) ABSTRACT

A method and apparatus for X-ray tube scanner automation using a 3D camera is disclosed. An RGBD image of a patient on a patient table is received from a 3D camera mounted on an X-ray tube. A transformation between a coordinate system of the 3D camera and a coordinate system of the patient table is calculated. A patient model is estimated from the RGBD image of the patient. The X-ray tube is automatically controlled to acquire an X-ray image of a region of interest of the patient based on the patient model.

36 Claims, 8 Drawing Sheets

302　　304　　306　　308

METHOD AND SYSTEM OF SCANNER AUTOMATION FOR X-RAY TUBE WITH 3D CAMERA

BACKGROUND OF THE INVENTION

The present invention relates to scanner automation for X-ray image acquisition, and more particularly, to X-ray tube scanner automation using a 3D camera.

X-ray scanning in typically performed by a technician manually positioning an X-ray tube to focus the X-ray scan on a region of interest on a patient. The positioning and orientation of the X-ray tube with respect to the patient relies on the technician's subjective decisions, which often leads to inconsistency between different X-ray scans. X-ray scanner automation is desirable due to multiple potential benefits. In addition to improved efficiency of the scanning workflow, X-ray scanner automation may also provide better scan quality as compared with X-ray scans obtained by technicians manually positioning the X-ray tube.

BRIEF SUMMARY OF THE INVENTION

The present invention provides a method and system for X-ray tube scanner automatic using a 3D camera. Embodiments of the present invention utilize RGBD (red, green, blue, and depth) images obtained from a 3D camera mounted on an X-ray tube to perform scanner automation of the X-ray tube. Embodiments of the present invention generate a patient model from the RGBD images using a machine learning-based method for body pose estimation, landmark detection, and body region estimation. Embodiments of the present invention automatically position the X-ray tube to perform an X-ray scan based on a region of interest of patient identified using the patient model.

In one embodiment of the present invention, an RGBD image of a patient on a patient table is received from a 3D camera mounted on an X-ray tube. A transformation between a coordinate system of the 3D camera and a coordinate system of the patient table is calculated. A patient model is estimated from the RGBD image of the patient. The X-ray tube is automatically controlled to acquire an X-ray image of a region of interest of the patient based on the patient model.

These and other advantages of the invention will be apparent to those of ordinary skill in the art by reference to the following detailed description and the accompanying drawings.

DETAILED DESCRIPTION

The present invention relates to a method and system of X-ray tube scanner automation using a 3D camera. Embodiments of the present invention are described herein to give a visual understanding of the scanner automation method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention generate a personalized 3D mesh model of a person that estimates the detailed body pose as well as the shape of the person from RGB-D image data obtained from a depth camera, such as a Microsoft Kinect depth camera. Such a personalized 3D mesh model of a person is referred to herein as an avatar. Unlike other approaches to obtain a personalized mesh from multiple sensors of video sequences, embodiments of the present invention generate a personalized mesh from a single snapshot from a depth camera that captures a partial view of the person and deals with body clothing. Embodiments of the present invention provide reconstruction of a detailed body shape (mesh) even from a partial view of the body, body shape estimation from a single snapshot from any depth camera sensor, body shape estimation of the person under the clothing, and appropriate sensor noise statistics modeling to obtain precise body pose and shape.

3D cameras are cameras that provide depth information along with typical image information, such as RGB (Red, Green, Blue) data. A 3D camera can be a structured light based camera (such as Microsoft Kinect or ASUS Xtion), a stereo camera, or a time of flight camera (such as Creative TOF camera). The image data obtained from a depth camera is typically referred to as an RGBD (RGB+Depth) image, which includes an RGB image, in which each pixel has an RGB value, and a depth image, in which the value of each pixel corresponds to a depth or distance of the pixel from the camera. Embodiments of the present invention utilize a 3D camera for X-ray tube scanner automation. Embodiments of the present invention utilize a machine learning-based method to localize body landmarks in an RGBD image obtained using a 3D camera. Embodiments of the present invention utilize a 3D camera mounted on an X-ray tube to acquire the RGBD image data. Due to the mobility of the X-ray tube, embodiments of the present invention utilize a marker-based registration solution to provide for automatic extrinsic calibration between multiple coordinate systems.

Figure 1:
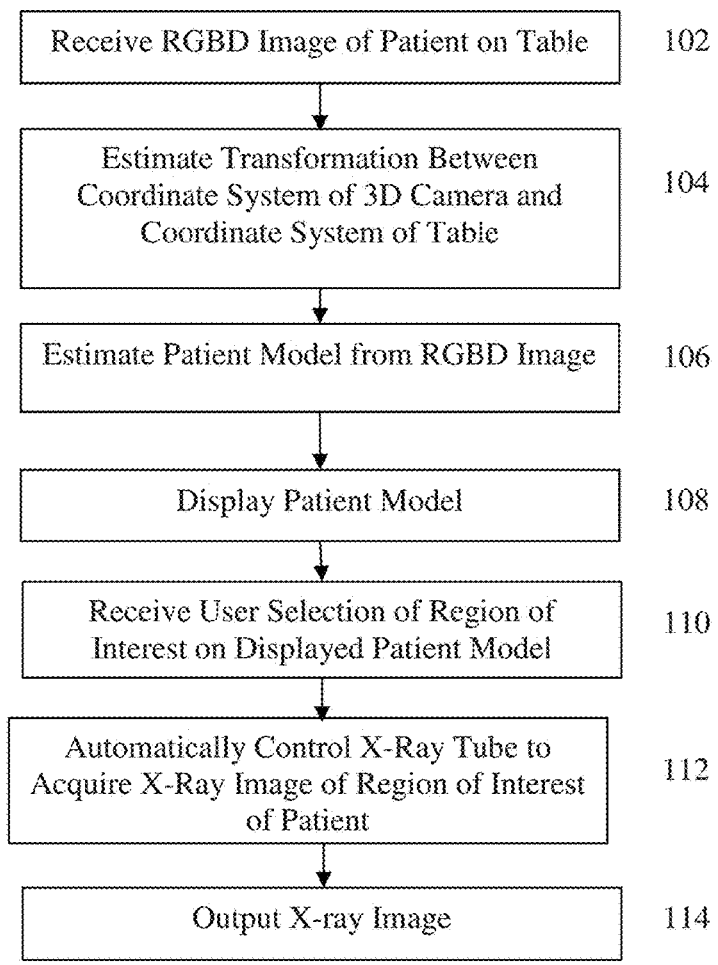
FIG. 1 illustrates a method for X-ray tube scanner automation according to an embodiment of the present invention.
Figure 2A:
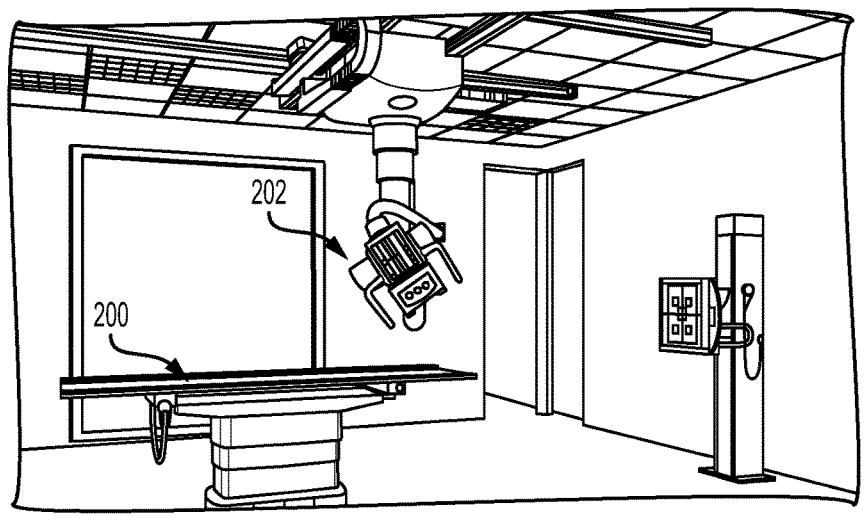
FIGS. 2A and 2B X-ray tube scanning apparatus according to an embodiment of the present invention.
Figure 2B:
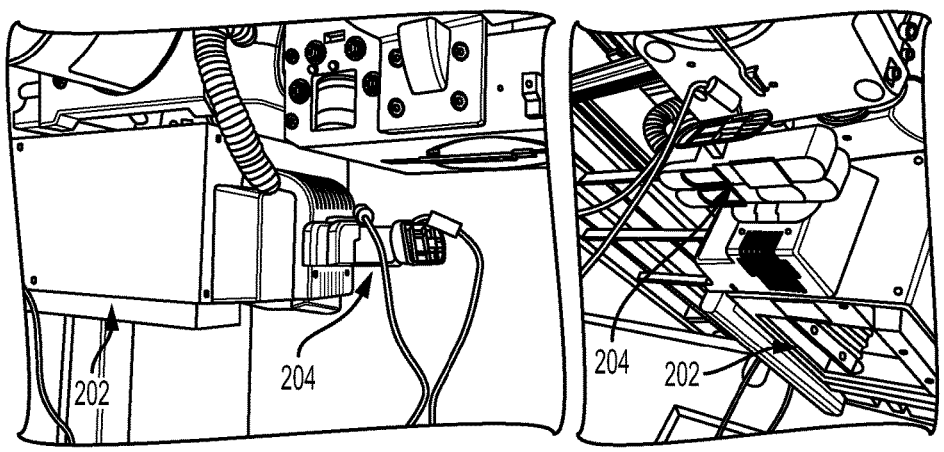

FIG. 1 illustrates a method for X-ray tube scanner automation according to an embodiment of the present invention. The method of FIG. 1 transforms RGBD image data of a patient to generate a patient model and performs automated positioning of an X-ray tube to acquire X-ray images of a region of interest of the patient. At step 102, RGBD image data of a patient on a table is received from a 3D camera. FIGS. 2A and 2B X-ray tube scanning apparatus according to an embodiment of the present invention. As shown in FIG. 2A, the X-ray scanning apparatus includes a patient table 200 and an X-ray tube 202. The X-ray tube 202 has five degrees of freedom to move with respect to the patient table 200 and a patient on the patient table 200. This allows the X-ray tube 202 to move to different positions and orientations to capture x-ray images of target regions of a patient on the table 200. As shown in FIG. 2B, a 3D camera 204 is mounted on the X-ray tube 202. For example, the 3D camera 204 can be attached to a rear side of the X-ray 202 as shown in FIG. 2B, but the present invention is not limited thereto. A computer, such as the computer shown in FIG. 7 and described below, communicates with the X-ray tube 202 and the 3D camera 204 to control the operations of the X-ray tube 202 and the 3D camera 204.

Once the patient is positioned on the patient table, an RGBD image of the patient is acquired using the 3D camera. In a possible implementation, the RGBD image can be acquired in response to an input received from user (e.g., a technician), such as the user pressing a trigger button. In one embodiment, the X-ray to can be automatically moved to a predetermined location prior to acquiring the RGBD image using the 3D camera mounted on the X-ray tube. For example, the X-ray tube can be moved a highest position above the table (along a z axis) and can be centered relative to the width and length of the table (x and y axes) to ensure that the patient on the table is in a field of view of the 3D camera. This can be a coarse movement and the X-ray tube need not be positioned in a precise location or with a particular orientation, as marker-based image registration will be used to calibrate the RGBD image to the coordinate system of the table. In another embodiment, the RGBD image can be acquired without first moving the X-ray tube to a predetermined location. In this case it can be determined if enough table markers (described below) are visible in the RGBD image for the RGBD image to be registered to the coordinate system of the table, and if not, the X-ray tube can be re-positioned and another RGBD image can be acquired.

Figure 3:
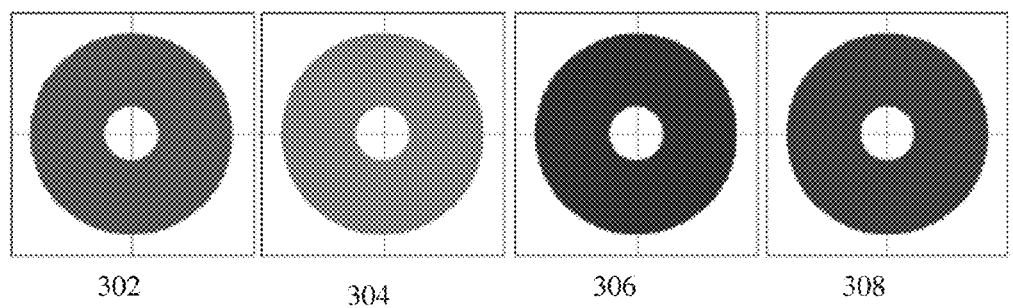
FIG. 3 illustrates a set of four ring markers arranged in a predetermined pattern according to an embodiment of the present invention.
Figure 4:
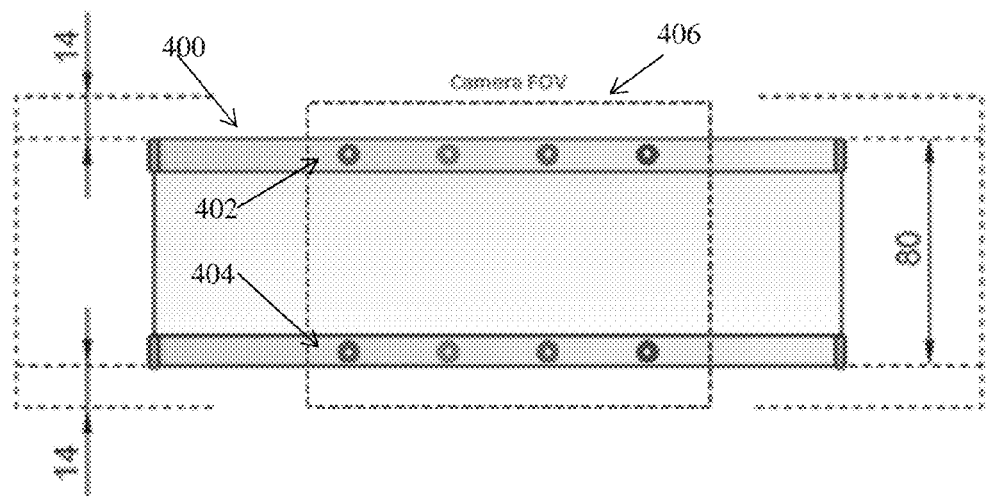
FIG. 4 illustrates ring marker placement on the patient table according to an embodiment of the present invention.

Returning to FIG. 1, at step 104, a transformation between a coordinate system of the 3D camera and a coordinate system of the patient table is calculated. In a first embodiment, the transformation between the coordinate system of the 3D camera and the coordinate system of the patient table is calculated by detecting table markers in the RGBD image and the estimating the transformation between the coordinate system of the 3D camera and the coordinate system of the patient table based on the detected table markers in the RGBD image. One challenge of mounting the 3D camera on the X-ray tube is that the 3D camera's position will not remain constant with respect to the patient table and the scanning room coordinate system. According to an advantageous embodiment of the present invention, by assuming that the patient table is at least partially visible in the 3D camera's field of view, the patient table is equipped with colored ring markers that are used for automatic registration between multiple coordinate systems. FIG. 3 illustrates a set of four ring markers 302, 304, 306, and 308 arranged in a predetermined pattern according to an embodiment of the present invention. Although shown in black and white in FIG. 3, each ring marker 302, 304, 306, and 308 has a distinctive color in its outer ring and is white in its inner circle. For example, in a possible arrangement, ring marker 302 has a red outer circle, ring marker 304 has a green outer circle, ring marker 306 has a blue outer circle, and ring marker 308 has a black outer circle. FIG. 4 illustrates ring marker placement on the patient table according to an embodiment of the present invention. As shown in FIG. 4, each side of the patient table 400 is has a set of ring markers 402 and 404, respectively. The ring markers in each set of ring markers 402 and 404 are arranged in the same predetermined pattern, such as the pattern shown in FIG. 3. Each ring marker is located in a specific predetermined location on the patient table and physical positions of the ring markers on the patient table are carefully measured so the markers can serve as a calibration pattern for camera pose estimation.

For ring marker detection, once the RGBD image is acquired a 3D Hough transform based method is used for robust circle detection in the RGBD image. In particular, a Hough transform is applied to the RGBD image to detect circular shapes in the RGBD image. The Hough transform uses gradient information extracted from the RGBD image and detects circular shapes in the RGBD image based on the gradient information. The brightness of the region inside the inner circle and the color distribution inside the outer ring of each ring marker are used to validate whether a detected circle in the 3D camera's field of view (i.e., in the RGBD image) is one of the four ring markers.

Once the ring markers are detected in the RGBD image, the transformation between the coordinate system of the 3D camera and the coordinate system of the patient table is estimated based on the detected ring markers in the RGBD image. The ring markers are arranged on the patient table in a predetermined specific positions to serve as a calibration pattern for estimating a pose of the 3D camera in the coordinate system of the patient table. Since the ring markers have distinctive colored outer rings and are arranged in a particular predetermined pattern on the patient table, each detected ring marker in the RGBD image can be uniquely identified. Thus, the pose estimation problem for estimating the pose of the 3D camera in the coordinate system of the patient table forms a standard PnP (Perspective-n-Point) problem that can be solved by calculating a transformation that aligns each detected ring marker in the RGBD image with the known location for that ring marker in the coordinate system of the patient table. Using this pose estimation, the acquired RGBD image data can be transformed to the patient table coordinate system to align the RGB image data with a camera field of view corresponding to a virtual camera at a fixed position (e.g., centered with respect to the length and width of the patient table) above the table. FIG. 4 shows the field of view 406 to which the acquired RGBD image data is aligned when the RGBD image data is transformed to the coordinate system of the patient table 400. A relative position of the 3D camera with respect to the X-ray tube can also be calibrated based on the transformation between the coordinate system of the 3D camera and the coordinate system of the patient table, as the relative position of the X-ray tube with respect to the patient table can be tracked.

In a second embodiment, tube position control parameters of a control system of the X-ray tube are received, and the transformation between the coordinate system of the 3D camera and the coordinate system of the patient table is calculated using a kinematic calibration based on the tube position control parameters of the control system of the X-ray tube. This embodiment enables automated control of the X-ray tube without the need for detecting the table markers. In an exemplary implementation, the tube position control parameters (which are described in greater detail below in connection with FIG. 7) can include three translational parameters and two rotational parameters to control a position and orientation of the X-ray tube. The tube position control parameters corresponding to a current position and orientation of the X-ray tube can be received from the control system of the X-ray tube and used in the kinematic calibration. The kinematic calibration calibrates the coordinate system of the 3D camera with the coordinate system of the patient table and coordinate systems of a kinematic chain of the X-ray tube control system. The kinematic calibration is described in greater detail below.

Figure 5:
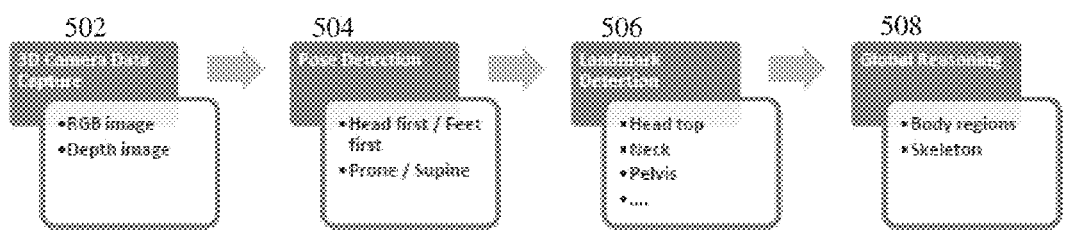
FIG. 5 illustrates a method for generating a patient model from an RGBD image of a patient according to an embodiment of the present invention.

Returning to FIG. 1, at step 106, a patient model is estimated from the RGBD image. FIG. 5 illustrates a method for generating a patient model from an RGBD image of a patient according to an embodiment of the present invention. The method of FIG. 5 can be used to implement step 108 of FIG. 1. Referring to FIG. 5, at step 502, the RGBD image data of the patient is captured using the 3D camera. This RGBD image data can be the same RGBD image data received in step 102 of FIG. 2. Alternatively, if once the pose of the 3D camera is estimated with respect to the coordinate system of the patient table, it is determined that the original RGBD image acquired in step 102 does not contain sufficient anatomy of the patient, the X-ray tube on which the 3D camera is mounted can be repositioned so more of the patient's anatomy is in the field of view of the 3D camera, and a new RGBD image can be acquired. The RGBD image includes an RGB image and a depth image. The color data in the RGB image and the depth (range) data in the depth image can be combined to represent the RGBD image data of the patient as a 3D point cloud.

Given the color and depth data represented as a 3D point cloud, an image region containing only the patient and the table is localized. The relative position of the 3D camera with respect to the X-ray tube scanner is known, as it is established during the calibration process, and the range of table movement is limited. This information is used as a spatial prior to automatically crop the image region enclosed by the 3D volume containing the patient and the table. This cropped data is then transformed such that the z-axis is aligned with the table surface normal and the x-y plane is aligned with the table surface. The transformed depth data (and associated color information) is then orthogonally projected on the x-y plane to generate a color and depth image pair referred to herein as the reprojected image, which is then used for subsequent processing. Next, to further refine the position and extent of the patient on the table, a machine-learning based full body detector can be applied on the reprojected image to detect an estimate of the patient position in the reprojected image. For this patient fully body detection, a Probabilistic Boosting Tree (PBT) with 2D Haar features extracted over reprojected depth and surface normal data can be trained and used as the full body detector. The PBT is trained using features extracted from annotated training data and the trained PBT is used to detect a coarse position of the patient in the reprojected image.

At step 504, pose detection is performed on the reprojected image to classify a pose of the patient. Given the coarse patient position information, the patient pose can be classified as head first versus feat first and classified as prone versus supine using one or more machine-learning based pose classifiers. Each of the pose classifiers can be a trained PBT classifier. According to an advantageous implementation, the PBT framework can be extended to multiple channels by considering Haar features extracted from the reprojected depth image, surface normal data, a saturation image, as well as U and V channels from LUV space. Fusing multiple channels can provide a significant improvement in pose detection over using depth information only.

According to an advantageous embodiment, instead of training a single multi-class classifier for pose detection, multiple binary classifiers can be trained to systematically handle the data variations. In an exemplary implementation, a head first vs. feet first classifier is applied to the reprojected image by considering half of the patient region that is close to the sensor (3D camera). This region covers the upper half of the body for the head first case and the lower half of the body for the feet first case. Once the patient is classified as head first or feet first in the reprojected image, a prone vs. supine classifier is applied to the reprojected image to classify the pose as either prone or supine. Separate prone/supine classifiers are trained for head first images and feet first images. Accordingly, which of the trained prone/supine classifiers is used to classify the pose of the patient in the reprojected image is determined based on whether the pose is classified as head first or feet first. This is because when a patient is laying on the table, the data statistics over the head region in the head first case are significantly different as compared to in the feet first case. This is due to the large angle between the 3D camera and the body surface as well as increasing data noise and the distance from the sensor increase.

At step 506, landmark detection is performed. Given the patient pose information, a sparse body surface model including a plurality of anatomical landmarks is fit to the reprojected image data. The body surface model can be represented as a Directed Acyclic Graph (DAG) over the anatomical landmarks on the body surface, where the graph captures the relative position of the landmarks with respect to each other. In an advantageous embodiment, the patient surface is modeled using 10 body landmarks—head, groin, and left and right landmarks for shoulders, waist, knees, and ankles. Respective landmark detectors are trained for each of the landmarks. For example, for each landmark, a multi-channel PBT classifier with Haar features extracted from the same channels as used to train the pose classifiers (e.g., reprojected depth image, surface normal data, saturation image, and U and V channels from Luv space) can be used to train each landmark detector. Due to camera and body surface angle, as well as sensor noise, the image statistics vary significantly over the body surface. The data distribution over a landmark in a head first case is different from that is a feet first case. Thus, in an advantageous embodiment, for each landmark, separate landmark detectors are trained for the head first and feet first poses. During landmark detection on the reprojected image, since the pose category is already detected, only one set of trained landmark detectors corresponding to the detected pose (head first or feet first) is applied.

The relative position of the landmarks is modeled as a Gaussian distribution whose parameters are obtained from annotations over a training data set. During landmark detection on the reprojected image, the trained landmark detectors are applied sequentially while taking contextual constraints of the neighboring landmarks into account. For each landmark, position hypotheses are obtained based on the trained landmark detector response as well as from previously detected landmarks in the DAG. In an exemplary implementation, given the position information for the patient, the groin landmark detection is performed first by applying the groin landmark detector in a center region of the patient. Next the knee landmark detectors are applied on an image region estimated based on constraints from the pose information as well as relative position information from the hypotheses from the groin region. One by one, landmark hypotheses are obtained for each landmark traversing the DAG.

At step 508, after all the landmark hypotheses for all the landmarks are obtained, a global reasoning is performed on the landmark hypotheses to obtain a set of landmarks with the highest joint likelihood based on the trained landmark detectors as well as the contextual information in the DAG. This sequential process of landmark detection handles the size and scale variations across patients of different ages. Once the final set of landmarks is detected using the global reasoning, body regions of the patient in the reprojected image can be defined based on the set of landmarks. For example, the reprojected image can be divided into body regions of head, torso, pelvis, upper leg, and lower leg. In a possible implementation, a human skeleton model can be fit the reprojected depth image based on the detected landmarks.

Returning to FIG. 1, at step 108, the patient model generated from the RGBD image is displayed. For example, the patient model can be displayed on a display screen of a computer or on a console of the X-ray scanner itself. The displayed patient model can show the reprojected image of the patient labeled with the detected body regions. The patient model can show boxes or cross points representing the positions of the detected landmarks. Alternatively, the displayed patient model can show a human skeleton model representing the patient's body.

Figure 6:
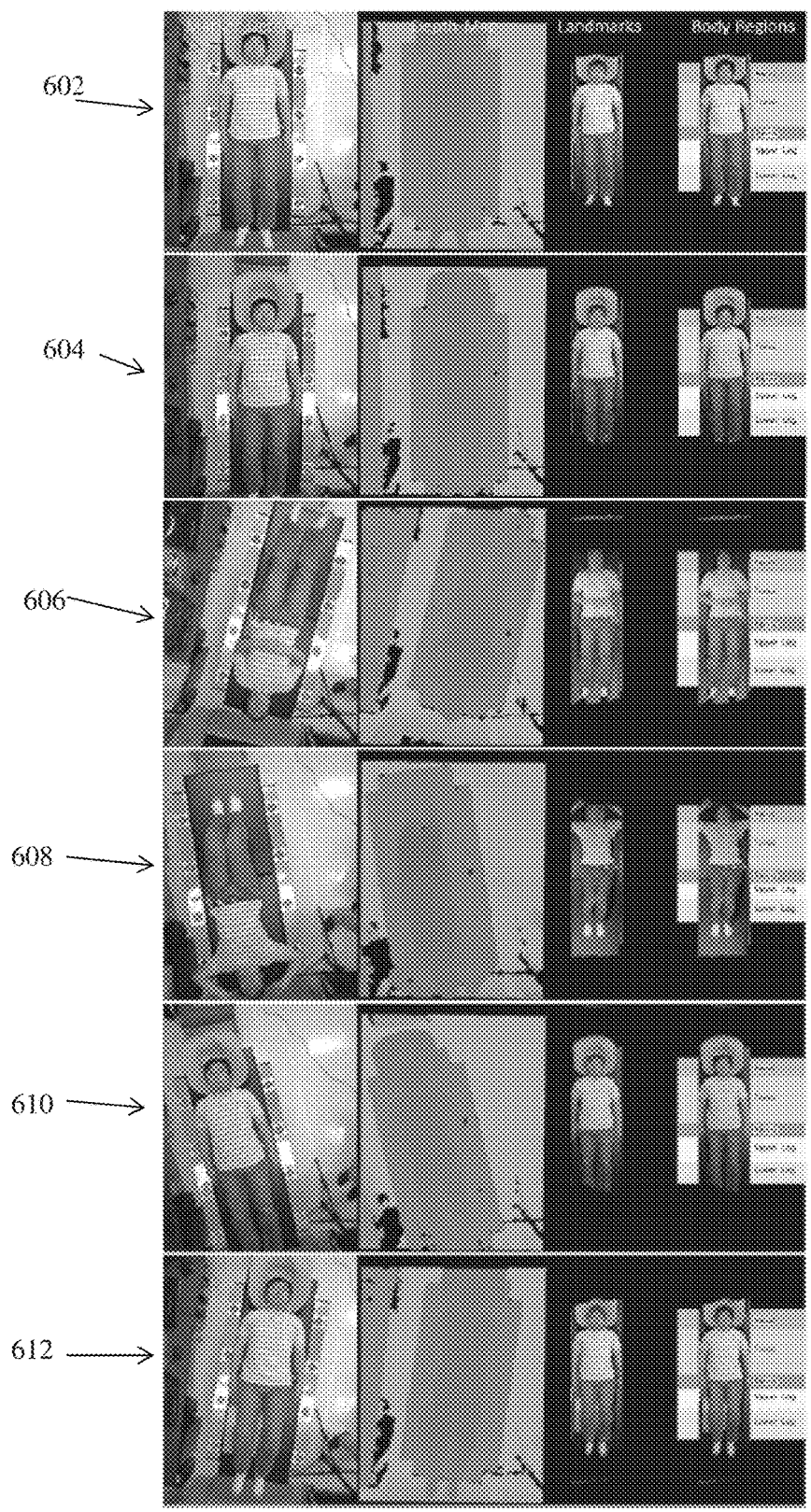
FIG. 6 illustrates exemplary patient modeling results.

FIG. 6 illustrates exemplary patient modeling results. The rows 602, 604, 606, 608, 610, and 612 of FIG. 6 show the results of marker detection, landmark detection, and body region estimation tasks successfully performed under different camera positions. The first column in each example 602, 604, 606, 608, 610, and 612 shows the initial RGB image and the detected ring markers on the patient table. The second column shows the depth map corresponding to the initial RGB image. The third column shows landmark detection results in the reprojected image of the patient. It can be observed that the reprojected image in each example 602, 604, 606, 608, 610, and 612 is aligned to the same field of view despite the differences in patient position and camera orientation in the initial RGB images and depth maps. The fourth column shows the reprojected image displayed with the estimated body regions (head, torso, pelvis, upper leg, and lower leg) based on the detected landmarks.

Returning to FIG. 1, at step 110, a user selection of a region of interest on the displayed patient model is received. For example, the user (e.g., technician), can select the region of interest of the patient by clicking on a target portion of the displayed patient model using a mouse, touchscreen, etc.

At step 112, the X-ray tube is automatically controlled to acquire the X-ray image of the region of interest. In particular, the position and orientation of the X-ray tube is automatically controlled to align the X-ray tube with the selected region of interest. In one embodiment, the X-ray tube can be automatically guided to be aligned with a particular target location because the relationships between the coordinate systems of the X-ray tube, the 3D camera, and the patient table were established either using the ring markers or the tube position control parameters of a control system of the X-ray tube. Once the X-ray tube is aligned with the selected region of interest, one or more X-ray images are acquired of the region of interest using the X-ray tube.

Figure 7:
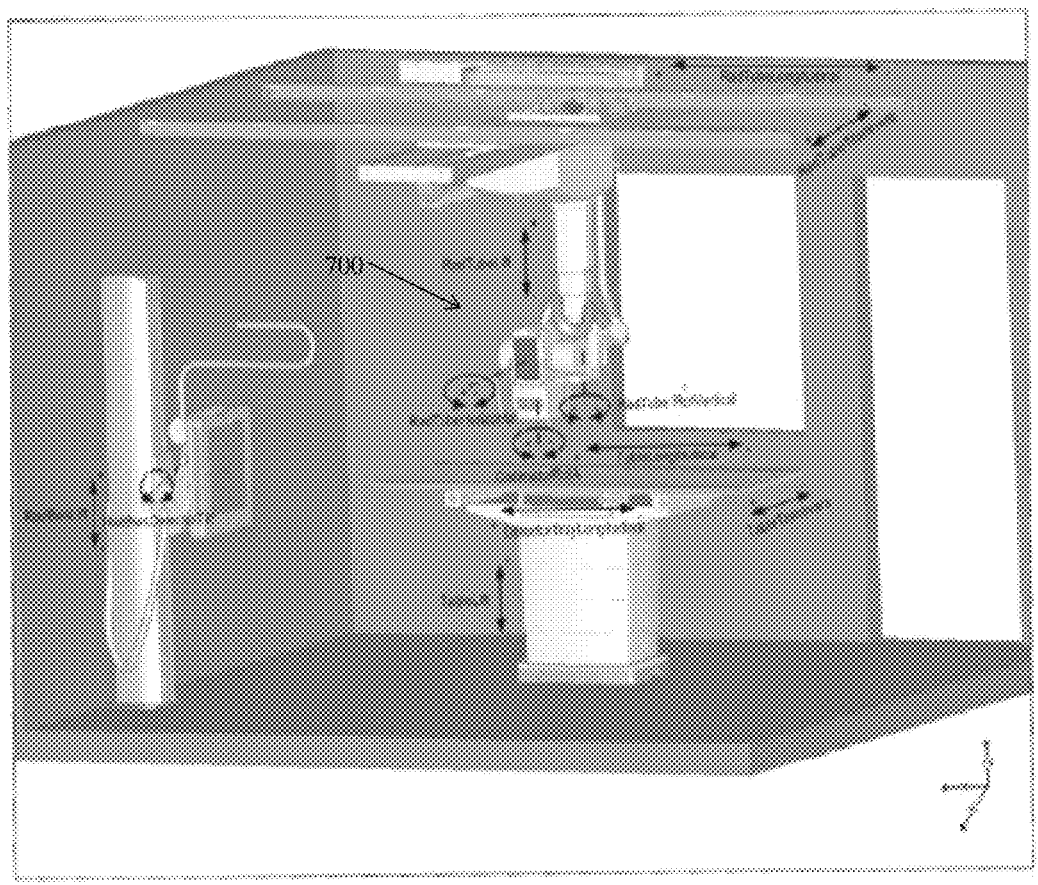
FIG. 7 illustrates control parameters of the X-ray tube scanner according to an embodiment of the present invention.

To carry out the X-ray tube scanner automation, the 3D position of the target region of interest must be transferred from the 3D camera coordinate system to the X-ray tube coordinate system. According to an advantageous embodiment of the present invention, inverse kinematics can be applied in order to determine joint angles and tube base positions for the X-ray tube control. To this end, kinematic calibration is used to establish a transformation between the 3D camera and the kinematic chain of the X-ray tube control system. As describe above, this kinematic calibration can also be used in step 104 of FIG. 1 to calculate the transformation between the coordinate system of the 3D camera and the coordinate system of the patient table. FIG. 7 illustrates control parameters of the X-ray tube scanner 700 according to an embodiment of the present invention. As shown in FIG. 7, based on the mechanical specification of the X-ray tube, there are five parameters for tube control including three translational parameters (TubeLongitudinal, TubeTransverse, and TubeLift) and two rotational parameters (RotVertical and RotHorizontal). It can be observed in FIG. 7 that the two rotational parameters (RotVertical and RotHorizontal) have different rotation centers.

Figure 8:
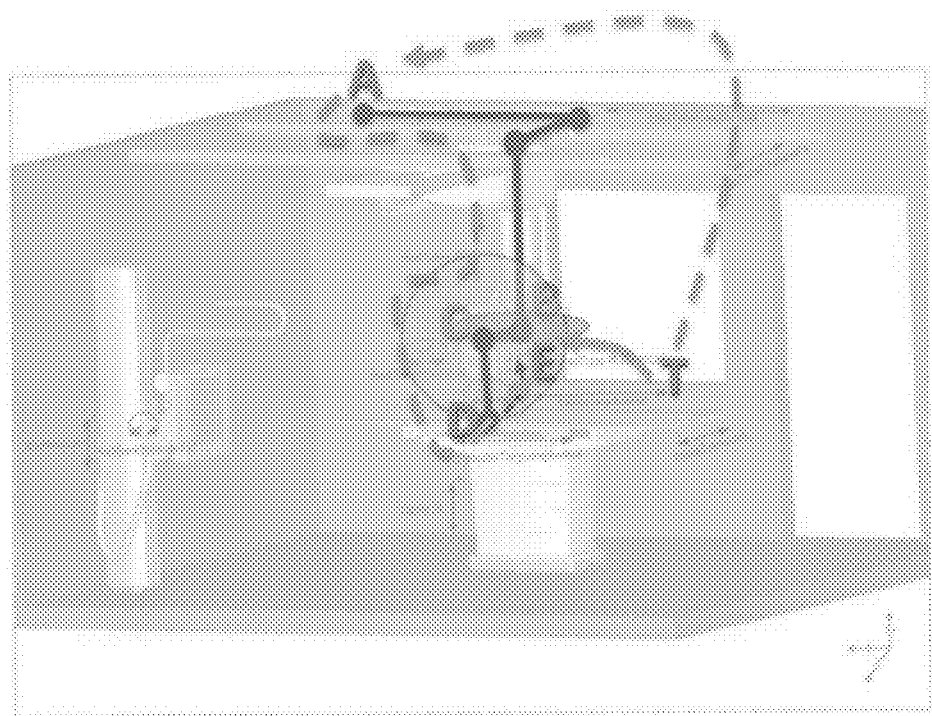
FIG. 8 illustrates a kinematic chain of X-ray tube control with a 3D camera.

As shown in FIG. 2B and discussed above, the 3D camera 204 can be attached to a rear side of the X-ray tube 202. This contributes an additional six degrees of freedom transform between the camera coordinate system with respect to the X-ray tube/collimator coordinate system. As the X-ray tube is not within the 3D camera's field of view, the ring markers are used to establish a link between the camera coordinate system and the X-ray tube coordinate system. As discussed above, the ring markers can be robustly detected and identified for camera pose estimation with respect to the table's coordinate system. This allows use to close the loop of kinematic chain of X-ray tube control. FIG. 8 illustrates a kinematic chain of X-ray tube control with a 3D camera. As shown in FIG. 8, the kinematic chain is as follows: Patient Table (T)→Tube Origin (A)→Tube Holder Vertical Rotation Center (B) →Tube Horizontal Rotation Center (C)→Collimator Light Field (D)→3D Camera (E) →Patient Table (T).

Given the current X-ray tube's position control parameters, the 3D camera's optical center and three axes can be transferred to the X-ray tube coordinate system with forward kinematics. More formally, for a 3D point $P_E$ in the camera coordinate system (E), its corresponding portion $P_A$ in the tube origin coordinate system (A) can be derived as follows:

$$P_A = \begin{bmatrix} R_V & t_s \\ 0 & 1 \end{bmatrix} \begin{bmatrix} R_H & t_{CB} \\ 0 & 1 \end{bmatrix} \begin{bmatrix} R_{ED} & t_{ED} \\ 0 & 1 \end{bmatrix} \quad (1)$$

$$P_E = \begin{bmatrix} R_{EA} & t_{EA} \\ 0 & 1 \end{bmatrix} P_E,$$

where $R_V$ is the 3×3 rotation matrix for RotVertical, $R_H$ is the rotation matrix for RotHorizontal, $t_s$ is the translation vector composed of three translational parameters (TubeLongitudinal, TubeTransverse, and TubeLift), $t_{CB}$ is the translational offset contributed from the arm connecting the two rotation centers (B) and (C), $R_{ED}$ and $t_{ED}$ represent the relative pose of the camera coordinate system (E) with respect to the collimator light field coordinate system (D), and $R_{EA}$ and $t_{EA}$ represent the relative pose of the camera coordinate system (E) with respect to the tube origin coordinate system (A).

In Equation (1), $R_V$, $R_H$, and $t_s$ can be derived from the five tube position control parameters. The vector $t_{CB}$ can be initialized with the tube arm length from the mechanical specification of the X-ray tube and can be further optimized if necessary. To calibrate the 6-DOF transform between the 3D camera and the X-ray collimator, $R_{ED}$ and $t_{ED}$, we take advantage of the fixed table coordinate system (T) defined by the colored ring markers placed on each side of the table. That is, $$P_A = \begin{bmatrix} R_V & t_s \\ 0 & 1 \end{bmatrix} \begin{bmatrix} R_H & t_{CB} \\ 0 & 1 \end{bmatrix} \begin{bmatrix} R_{ED} & t_{ED} \\ 0 & 1 \end{bmatrix} \begin{bmatrix} R_{TE} & t_{TE} \\ 0 & 1 \end{bmatrix} \quad (2)$$

$$P_T = \begin{bmatrix} R_{TA} & t_{TA} \\ 0 & 1 \end{bmatrix} P_T,$$

where $R_{TE}$ and $t_{TE}$ describe the 6-DOF transform between the table (T) and the 3D camera (E) that varies from frame to frame when there is any movement of the X-ray tube, and $R_{TA}$ and $t_{TA}$ represent the 6-DOF transform between the table (T) and the tube origin coordinate system (A). By rewriting Equation (2), we obtain:

$$P_E = \begin{bmatrix} R_{TE} & t_{TE} \\ 0 & 1 \end{bmatrix} \quad (3)$$

$$P_T = \left( \begin{bmatrix} R_V & t_s \\ 0 & 1 \end{bmatrix} \begin{bmatrix} R_H & t_{CB} \\ 0 & 1 \end{bmatrix} \begin{bmatrix} R_{ED} & t_{ED} \\ 0 & 1 \end{bmatrix} \right)^{-1} \begin{bmatrix} R_{TA} & t_{TA} \\ 0 & 1 \end{bmatrix} P_T.$$

With Equation (3), we are able to optimize the unknown parameters by minimizing the 3D position differences between the measures 3D ring marker locations and estimated locations:

$$\min_{t_{CB}, R_{ED}, R_{TA}, t_{TA}} \left\| P_E^{j,k} - \left( \begin{bmatrix} R_V^i & t_s^i \\ 0 & 1 \end{bmatrix} \begin{bmatrix} R_H^i & t_{CB} \\ 0 & 1 \end{bmatrix} \begin{bmatrix} R_{ED} & t_{ED} \\ 0 & 1 \end{bmatrix} \right)^{-1} \begin{bmatrix} R_{TA} & t_{TA} \\ 0 & 1 \end{bmatrix} P_T^k \right\|_2, \quad (4)$$

where $R_V^i$, $t_s^i$, and $R_H^i$ are derived from the tube position parameters in the i-th frame, $P_T^k$ is the k-th ring marker position in the table coordinate system, which can be directly measured from the 3D point cloud or transformed from the table coordinate system based on a robust perspective-n-point algorithm. That is, $$P_E^{j,k} = \begin{bmatrix} R_{TE}^i & t_{TE}^i \\ 0 & 1 \end{bmatrix} P_T^k. \quad (5)$$

In addition to minimizing 3D position errors, we can also minimize the 3D re-projection errors as well with the calibrated camera intrinsic parameters.

To further consider the situation where the collimator center (D in FIG. 8) may not be perfectly aligned with the tube horizontal rotation center (C in FIG. 8), an additional constraint can be added with the crosshair point of the light field projected from the collimator. The crosshair point, $P_E^{i,h}$, observed in the camera coordinate system, when transformed to the corresponding point in the collimator coordinate system by $$P_D^{j,h} = \begin{bmatrix} R_{ED} & t_{ED} \\ 0 & 1 \end{bmatrix} P_E^{j,h},$$

should approach the origin in the x and y axes of the collimator coordinate system.

With the relative pose between the camera and the collimator calibrated, the tube control parameters can now be manipulated for automated tube guidance using inverse kinematics. Using Equation (1), any point in the camera coordinate system can be transferred to the tube origin coordinate system with current tube control parameters to derive $R_{EA}$ and $t_{EA}$. The collimator coordinate system can be aligned with a specific point and surface orientation by minimizing the following equation:

$$\min_{R_V^*, R_H^*, t_s^*} \left\| \begin{bmatrix} R_{EA} & t_{EA} \\ 0 & 1 \end{bmatrix} \begin{bmatrix} R_{ME} & t_{ME} \\ 0 & 1 \end{bmatrix} P_M - \begin{bmatrix} R_V^* & t_s^* \\ 0 & 1 \end{bmatrix} \begin{bmatrix} R_H^* & t_{CB} \\ 0 & 1 \end{bmatrix} \begin{bmatrix} R_{MD} & t_{MD} \\ 0 & 1 \end{bmatrix} P_M \right\|_2, \quad (6)$$

where $P_M$ is a point in the target coordinate system, $R_{ME}$ and $t_{ME}$ represent the relative pose between the target coordinate system and the 3D camera, and $R_{MD}$ and $t_{MD}$ describe the desire orientation and distance of the points to be observed from the collimator. Depending on the use cases, it may be legitimate to align the collimator at multiple in-plane rotations to the target surface. Hence, the desired $R_{MD}$ and $t_{MD}$ can have multiple options that result in multiple plausible solutions to Equation (6). In practice, certain configurations may not be achievable due to the lack of one or more degrees of freedom of the tube control. Therefore, the optimal solution to Equation (6) can be selected by first removing solutions with large errors, and then examining the parameter distance from the current tube position and select the nearest one to save the time and effort of tube movement.

Returning the FIG. 1, at step 114, the X-ray image is output. Once the X-ray tube is automatically guided to a position and orientation corresponding to the selected region of interest and the region of interest of the patient is scanned by the X-ray tube to acquire an X-ray image. The X-ray image can be output by displaying the X-ray image on a display screen of a computer system, printing a physical copy of the X-ray image, and/or storing the X-ray image in memory or storage of a computer system.

Figure 9:
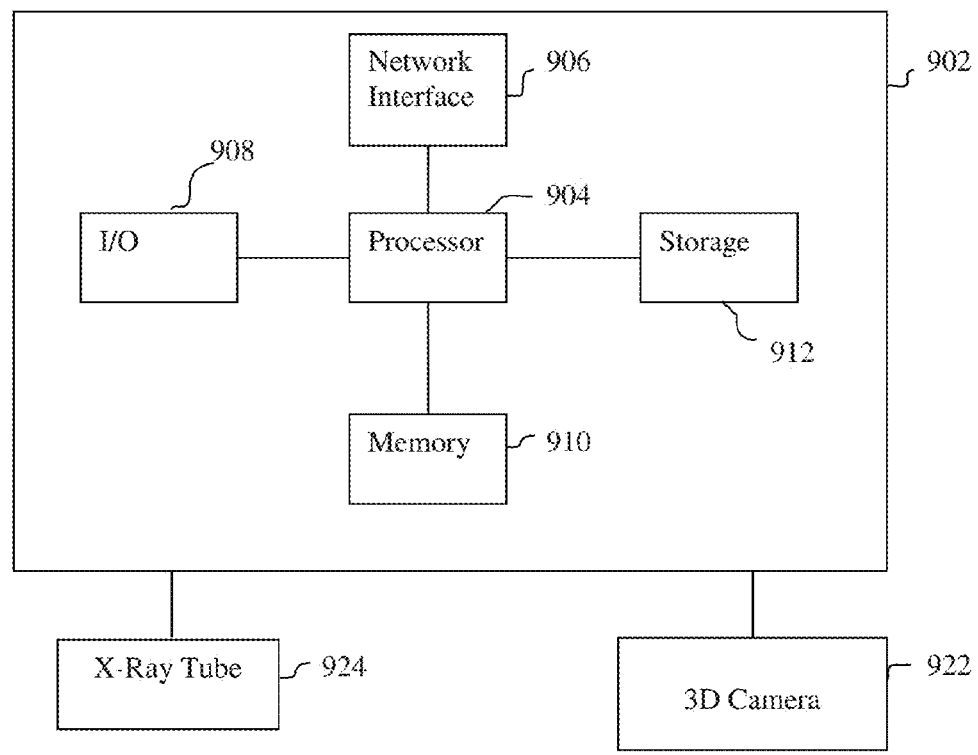
FIG. 9 is a high-level block diagram of a computer capable of implementing the present invention.

The above-described method for X-ray tube scanner automation using a 3D camera may be implemented on a computer using well-known computer processors, memory units, storage devices, computer software, and other components. A high-level block diagram of such a computer is illustrated in FIG. 9. Computer 902 contains a processor 904, which controls the overall operation of the computer 902 by executing computer program instructions which define such operation. The computer program instructions may be stored in a storage device 912 (e.g., magnetic disk) and loaded into memory 910 when execution of the computer program instructions is desired. Thus, the steps of the methods of FIGS. 1 and 5 may be defined by the computer program instructions stored in the memory 910 and/or storage 912 and controlled by the processor 904 executing the computer program instructions. A 3D camera 922 can be connected to the computer 902 to input RGBS image data to the computer 902. The 3D camera 922 and the computer 902 may be directly connected or may communicate wirelessly through a network or other wireless communication protocol. An X-ray tube scanner 924 can also be connected to the computer 902. The X-ray tube scanner 924 and the computer 902 may be directly connected or may communicate through a network or other wireless communication protocol. It is also possible to implement the medical image acquisition device and the computer 902 as one device. The computer 902 can communicate with the X-ray tube scanner 924 to control the positioning and orientation of the X-ray tube 924 and to control X-ray image acquisition by the X-ray tube 924. X-ray images acquired by the X-ray tube scanner 924 can be input to the computer 902. The computer 902 also includes one or more network interfaces 906 for communicating with other devices via a network. The computer 902 also includes other input/output devices 908 that enable user interaction with the computer 902 (e.g., display, keyboard, mouse, speakers, buttons, etc.). Such input/output devices 908 may be used in conjunction with a set of computer programs as an annotation tool to annotate volumes received from the image acquisition device 920. One skilled in the art will recognize that an implementation of an actual computer could contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for X-ray tube scanner automation, comprising:
    receiving an RGBD image of a patient on a patient table from a 3D camera mounted on an X-ray tube;
    calculating a transformation between a coordinate system of the 3D camera and a coordinate system of the patient table;
    estimating a patient model from the RGBD image of the patient; and
    automatically controlling the X-ray tube to acquire an X-ray image of a region of interest of the patient based on the patient model,
    wherein estimating a patient model from the RGBD image of the patient comprises:
    detecting a patient pose in the RGBD image using one or more machine learning-based pose classifiers;
    detecting anatomical landmarks of the patient in the RGBD data based on the detected patient pose.

2. The method of claim 1, wherein calculating a transformation between a coordinate system of the 3D camera and a coordinate system of the patient table comprises:
    detecting table markers on the patient table in the RGBD image; and
    estimating the transformation between the coordinate system of the 3D camera and the coordinate system of the patient table based on the detected table markers in the RGBD image.

3. The method of claim 2, wherein the table markers on the patient table comprise a respective set of ring markers on opposite sides of the patient table with each set of ring markers having a number of rings each having an outer ring of a distinctive color and a white inner circle.

4. The method of claim 3, wherein detecting table markers on the patient table in the RGBD image comprises:
    detecting circular shapes in the RGBD image using a 3D Hough transform; and
    determining whether the detected circular shapes in the RGBD image match one of the ring markers on the patient table based a brightness of the inner circle and a color distribution inside the outer ring.

5. The method of claim 1, wherein estimating a patient model from the RGBD image of the patient comprises:
    transforming a 3D point cloud representation of the RGBD image to align the RGBD image with a predetermined field of view of the patient table using the estimated transformation between the coordinate system of the 3D camera and the coordinate system of the patient table;
    projecting the 3D point cloud representation to generate a reprojected image comprising a color and depth image pair; and
    estimating the patient model using the reprojected image.

6. The method of claim 1, wherein detecting a patient pose in the RGBD image using one or more machine learning-based pose detector comprises:
    classifying the patient pose as head first or feet first using a first trained pose classifier; and
    classifying the patient pose as prone or supine using one of a second trained pose classifier or a third trained pose classifier based on the classification of the patient pose as head first or feet first by the first trained pose classifier.

7. The method of claim 6, wherein each of the first, second and, third trained pose classifiers is a multi-channel probabilistic boosting tree (PBT) classifier that extracts Haar features from a plurality of image channels associated with the RGBD image.

8. The method of claim 1, wherein detecting anatomical landmarks of the patient in the RGBD data based on the detected patient pose comprises:
    detecting each of a plurality of landmarks a directed acyclic graph (DAG) using respective machine learning-based landmark detectors for each of the plurality of landmarks based on relative positons of the plurality of anatomical landmarks in the DAG, wherein for each of the plurality of landmarks, the machine learning-based landmark detector is selected from a first trained landmark detector and trained landmark detector based on a classification of the patient pose as head first or feet first.

9. The method of claim 8, wherein each of the machine learning-based landmark detectors for the plurality of landmarks is a multi-channel probabilistic boosting tree (PBT) classifier that extracts Haar features from a plurality of image channels associated with the RGBD image.

10. The method of claim 1, wherein estimating a patient model from the RGBD image of the patient further comprises:
    prior to classifying the patient pose, estimating a coarse position of the patient in the RGBD image using a machine learning-based full body detector.

11. The method of claim 1, wherein estimating a patient model from the RGBD image of the patient further comprises:
    estimating a plurality of body regions of the patient based on the detected anatomical landmarks.

12. The method of claim 1, wherein estimating a patient model from the RGBD image of the patient further comprises:

fitting a human skeleton model to the RGBD image based on the detected anatomical landmarks.

13. The method of claim 1, further comprising:
displaying the estimated patient model on a display device; and
receiving a user input of the region of interest of the patient on the displayed patient model.

14. The method of claim 1, wherein calculating a transformation between a coordinate system of the 3D camera and a coordinate system of the patient table comprises:
receiving tube position control parameters of a control system of the X-ray tube; and
calculating a transformation between the coordinate system of the 3D camera and the coordinate system of the patient table using a kinematic calibration based on the tube position control parameters of the control system of the X-ray tube.

15. The method of claim 14, wherein the kinematic calibration calibrates the coordinate system of the 3D camera, the coordinate system of the patient table, and coordinate systems of a kinematic chain of the X-ray tube control system.

16. The method of claim 15, wherein the kinematic chain of the X-ray tube control system includes a tube origin, a tube holder vertical rotation center, a tube horizontal rotation center, and a collimator light field.

17. The method of claim 14, wherein automatically controlling the X-ray tube to acquire an X-ray image of a region of interest of the patient based on the patient model comprises:
automatically adjusting the tube position control parameters of the control system of the X-ray tube to guide the X-ray tube to a target position and orientation in a coordinate system of the X-ray tube corresponding to the region interest on the estimated patient model in the coordinate system of the 3D camera using inverse kinematics based on the kinematic calibration.

18. The method of claim 17, wherein the tube position control parameters of the control system of the X-ray tube comprise three translational parameters and two rotational parameters.

19. An apparatus for X-ray tube scanner automation, comprising:
means for receiving an RGBD image of a patient on a patient table from a 3D camera mounted on an X-ray tube;
means for calculating a transformation between a coordinate system of the 3D camera and a coordinate system of the patient table;
means for estimating a patient model from the RGBD image of the patient; and
means for automatically controlling the X-ray tube to acquire an X-ray image of a region of interest of the patient based on the patient model
wherein the means for calculating a transformation between a coordinate system of the 3D camera and a coordinate system of the patient table comprises:
means for detecting table markers on the patient table in the RGBD image; and
means for estimating the transformation between the coordinate system of the 3D camera and the coordinate system of the patient table based on the detected table markers in the RGBD image.

20. The apparatus of claim 19, wherein the table markers on the patient table comprise a respective set of ring markers on opposite sides of the patient table with each set of ring markers having a number of rings each having an outer ring of a distinctive color and a white inner circle.

21. The apparatus of claim 19, wherein the means for estimating a patient model from the RGBD image of the patient comprises:
means for detecting a patient pose in the RGBD image using one or more machine learning-based pose classifiers;
means for detecting anatomical landmarks of the patient in the RGBD data based on the detected patient pose.

22. The apparatus of claim 19, further comprising:
means for displaying the estimated patient model on a display device; and
means for receiving a user input of the region of interest of the patient on the displayed patient model.

23. The apparatus of claim 19, wherein the means for calculating a transformation between a coordinate system of the 3D camera and a coordinate system of the patient table comprises:
means for calculating a transformation between the coordinate system of the 3D camera and the coordinate system of the patient table using a kinematic calibration based on tube position control parameters of a control system of the X-ray tube.

24. The apparatus of claim 23, wherein the means for automatically controlling the X-ray tube to acquire an X-ray image of a region of interest of the patient based on the patient model comprises:
means for automatically adjusting the tube position control parameters of the control system of the X-ray tube to guide the X-ray tube to a target position and orientation in a coordinate system of the X-ray tube corresponding to the region interest on the estimated patient model in the coordinate system of the 3D camera using inverse kinematics based on the kinematic calibration.

25. A non-transitory computer readable medium storing computer program instructions for X-ray tube scanner automation, the computer program instructions when executed by a processor cause the processor to perform operations comprising:
receiving an RGBD image of a patient on a patient table from a 3D camera mounted on an X-ray tube;
calculating a transformation between a coordinate system of the 3D camera and a coordinate system of the patient table;
estimating a patient model from the RGBD image of the patient; and
automatically controlling the X-ray tube to acquire an X-ray image of a region of interest of the patient based on the patient model,
wherein calculating a transformation between a coordinate system of the 3D camera and a coordinate system of the patient table comprises:
receiving tube position control parameters of a control system of the X-ray tube; and
calculating a transformation between the coordinate system of the 3D camera and the coordinate system of the patient table using a kinematic calibration based on the tube position control parameters of the control system of the X-ray tube.

26. The non-transitory computer readable medium of claim 25, wherein calculating a transformation between a coordinate system of the 3D camera and a coordinate system of the patient table comprises:
detecting table markers on the patient table in the RGBD image; and estimating the transformation between the coordinate system of the 3D camera and the coordinate system of the patient table based on the detected table markers in the RGBD image.

27. The non-transitory computer readable medium of claim 26, wherein the table markers on the patient table comprise a respective set of ring markers on opposite sides of the patient table with each set of ring markers having a number of rings each having an outer ring of a distinctive color and a white inner circle.

28. The non-transitory computer readable medium of claim 27, wherein detecting table markers on the patient table in the RGBD image comprises:
    detecting circular shapes in the RGBD image using a 3D Hough transform; and
    determining whether the detected circular shapes in the RGBD image match one of the ring markers on the patient table based a brightness of the inner circle and a color distribution inside the outer ring.

29. The non-transitory computer readable medium of claim 25, wherein estimating a patient model from the RGBD image of the patient comprises:
    detecting a patient pose in the RGBD image using one or more machine learning-based pose classifiers;
    detecting anatomical landmarks of the patient in the RGBD data based on the detected patient pose.

30. The non-transitory computer readable medium of claim 29, wherein detecting a patient pose in the RGBD image using one or more machine learning-based pose detector comprises:
    classifying the patient pose as head first or feet first using a first trained pose classifier; and
    classifying the patient pose as prone or supine using one of a second trained pose classifier or a third trained pose classifier based on the classification of the patient pose as head first or feet first by the first trained pose classifier.

31. The non-transitory computer readable medium of claim 29, wherein detecting anatomical landmarks of the patient in the RGBD data based on the detected patient pose comprises:
    detecting each of a plurality of landmarks a directed acyclic graph (DAG) using respective machine learning-based landmark detectors for each of the plurality of landmarks based on relative positons of the plurality of anatomical landmarks in the DAG, wherein for each of the plurality of landmarks, the machine learning-based landmark detector is selected from a first trained landmark detector and trained landmark detector based on a classification of the patient pose as head first or feet first.

32. The non-transitory computer readable medium of claim 29, wherein estimating a patient model from the RGBD image of the patient further comprises:
    prior to classifying the patient pose, estimating a coarse position of the patient in the RGBD image using a machine learning-based full body detector.

33. The non-transitory computer readable medium of claim 29, wherein estimating a patient model from the RGBD image of the patient further comprises:
    estimating a plurality of body regions of the patient based on the detected anatomical landmarks.

34. The non-transitory computer readable medium of claim 29, wherein estimating a patient model from the RGBD image of the patient further comprises:
    fitting a human skeleton model to the RGBD image based on the detected anatomical landmarks.

35. The non-transitory computer readable medium of claim 25, wherein the operations further comprise:
    displaying the estimated patient model on a display device; and
    receiving a user input of the region of interest of the patient on the displayed patient model.

36. The non-transitory computer readable medium of claim 25, wherein automatically controlling the X-ray tube to acquire an X-ray image of a region of interest of the patient based on the patient model comprises:
    automatically adjusting the tube position control parameters of the control system of the X-ray tube to guide the X-ray tube to a target position and orientation in a coordinate system of the X-ray tube corresponding to the region interest on the estimated patient model in the coordinate system of the 3D camera using inverse kinematics based on the kinematic calibration.

* * * * *